United States Patent
Xiao et al.

(10) Patent No.: US 11,690,599 B2
(45) Date of Patent: Jul. 4, 2023

(54) VOLUME ACQUISITION METHOD FOR OBJECT IN ULTRASONIC IMAGE AND RELATED ULTRASONIC SYSTEM

(71) Applicant: QISDA CORPORATION, Taoyuan (TW)

(72) Inventors: Wei-Ting Xiao, Taoyuan (TW); Yu-Teng Tung, Hsinchu (TW)

(73) Assignee: Qisda Corporation, Taoyuan (TW)

(\*) Notice: Subject to any disclaimer, the term of this patent is extended or adjusted under 35 U.S.C. 154(b) by 181 days.

(21) Appl. No.: 17/243,584

(22) Filed: Apr. 29, 2021

(65) Prior Publication Data
US 2022/0087649 A1 Mar. 24, 2022

(30) Foreign Application Priority Data
Sep. 18, 2020 (CN) .......................... 202010986534.1

(51) Int. Cl.
*G06T 7/136* (2017.01)
*A61B 8/08* (2006.01)
(Continued)

(52) U.S. Cl.
CPC .............. *A61B 8/483* (2013.01); *A61B 8/463* (2013.01); *G06T 5/40* (2013.01); *G06T 7/12* (2017.01);
(Continued)

(58) Field of Classification Search
CPC .... G06T 7/10; G06T 7/12; G06T 7/13; G06T 7/136; G06T 7/149; G06T 7/187;
(Continued)

(56) References Cited

U.S. PATENT DOCUMENTS

| 8,369,590 B2\* | 2/2013 | Wang | G06T 7/174 |
| | | | 382/128 |
| 2016/0007970 A1\* | 1/2016 | Dufour | A61B 8/085 |
| | | | 600/437 |

(Continued)

OTHER PUBLICATIONS

Narra, Ravi Teja, et al. "Automated ovarian volume quantification in transvaginal ultrasound." 2018 IEEE 15th International Symposium on Biomedical Imaging (ISBI 2018). IEEE, 2018. (Year: 2018).\*

(Continued)

*Primary Examiner* — Ian L Lemieux (57) ABSTRACT

An object volume acquisition method of an ultrasonic image, for a probe of an ultrasonic system is disclosed. The volume acquisition method of the object in the ultrasonic image includes collecting, by the probe, a plurality of two-dimensional ultrasonic images; obtaining the plurality of two-dimensional ultrasonic images, an offset angle, a rotation axis and a frequency of the probe corresponding to the plurality of two-dimensional ultrasonic images; segmenting a first image including an ultrasonic image object from each two-dimensional ultrasonic image of the plurality of two-dimensional ultrasonic images based on a deep learning structure; determining a contour of the ultrasonic image object; reconstructing a three-dimensional model corresponding to the ultrasonic image object according to the contour of the ultrasonic image object corresponding to the each two-dimensional ultrasonic image; and calculating a volume of the ultrasonic image object according to the three-dimensional model corresponding to the ultrasonic image object.

10 Claims, 5 Drawing Sheets

(51) Int. Cl.
 *A61B 8/00* (2006.01)
 *G06T 7/12* (2017.01)
 *G06T 7/149* (2017.01)
 *G06T 5/40* (2006.01)

(52) U.S. Cl.
 CPC .............. *G06T 7/136* (2017.01); *G06T 7/149* (2017.01); *G06T 2207/10132* (2013.01); *G06T 2207/20084* (2013.01); *G06T 2207/30004* (2013.01)

(58) Field of Classification Search
 CPC ........... G06T 7/194; G06T 2207/20081; G06T 2207/20084; G06T 2207/10132; G06T 5/40; G06T 2207/30004–30104; G06N 3/02–088; A61B 8/483; A61B 8/463; A61B 5/055; A61B 6/032; A61B 6/5205; A61B 6/5217; A61B 8/4254; A61B 8/5223; A61B 8/5207; A61B 8/5215
 See application file for complete search history.

(56) References Cited

U.S. PATENT DOCUMENTS

| | | | |
|---|---|---|---|
| 2016/0058422 A1* | 3/2016 | Lee | A61B 8/483 600/443 |
| 2021/0267570 A1* | 9/2021 | Ulman | A61B 8/5223 |
| 2022/0304653 A1* | 9/2022 | Smistad | A61B 8/463 |

OTHER PUBLICATIONS

Qiu, Wu, et al. "Rotationally resliced 3D prostate TRUS segmentation using convex optimization with shape priors." Medical physics 42.2 (2015): 877-891. (Year: 2015).*
Gonzalez, Rafael C., and R. E. Woods. "Digital image processing." Pearson, 3rd ed., pp. 122-129, 2008. (Year: 2008).*
Du, Getao, et al. "Medical image segmentation based on u-net: A review." Journal of Imaging Science and Technology 64 (2020): 1-12. (Year: 2020).*
Huang, Qinghua, et al. "Segmentation of breast ultrasound image with semantic classification of superpixels." Medical Image Analysis 61 (2020): 101657. (Year: 2020).*
Orlando, Nathan, et al. "Automatic prostate segmentation using deep learning on clinically diverse 3D transrectal ultrasound images." Medical physics 47.6 (2020): 2413-2426. (Year: 2020).*

* cited by examiner

VOLUME ACQUISITION METHOD FOR OBJECT IN ULTRASONIC IMAGE AND RELATED ULTRASONIC SYSTEM

BACKGROUND OF THE INVENTION

1. Field of the Invention

The present invention relates to a volume acquisition method for object in ultrasonic image and related ultrasonic system, and more particularly, to a volume acquisition method for object in ultrasonic image and related ultrasonic system capable of establishing a three-dimensional model with a deep learning structure to efficiently and accurately calculate the volume of the object in the ultrasonic image.

2. Description of the Prior Art

Conventional imaging techniques in the medical field, e.g. magnetic resonance imaging (MRI), computed tomography (CT) scanning and ultrasonic three-dimensional imaging techniques, can clearly and efficiently obtain images with non-invasive methods to precisely calculate or estimate a volume of an object in the images, and thus the conventional imaging techniques are widely utilized in medical examinations. The conventional medical techniques estimate the volume of the object in an ultrasonic image based on length, width, height of the object. However, an error occurs when the above conventional medical techniques perform an image capturing, an image segmentation and a volume calculation, e.g. a bladder of a subject is deformed because of the extrusion of a device, the bladder extents towards both sides and squeezes adjacent organs, which makes a shape of the bladder a non-oval shape, and causes error in volume estimation. A urine volume in the bladder cannot be precisely estimated accordingly. Therefore, improvements are necessary to the conventional technique.

SUMMARY OF THE INVENTION

The present invention provides a volume acquisition method for an object in ultrasonic image and related ultrasonic system to accurately calculate the volume of the ultrasonic image object based on deep learning structure.

An embodiment of the present invention discloses an object volume acquisition method of an ultrasonic image, for a probe of an ultrasonic system, wherein the volume acquisition method of the object in the ultrasonic image comprises collecting, by the probe, a plurality of two-dimensional ultrasonic images; obtaining the plurality of two-dimensional ultrasonic images, an offset angle, a rotation axis and a frequency of the probe corresponding to the plurality of two-dimensional ultrasonic images; segmenting a first image including an ultrasonic image object from each two-dimensional ultrasonic image of the plurality of two-dimensional ultrasonic images based on a deep learning structure; determining a contour of the ultrasonic image object according to the first image corresponding to the each two-dimensional ultrasonic image; reconstructing a three-dimensional model corresponding to the ultrasonic image object according to the contour of the ultrasonic image object corresponding to the each two-dimensional ultrasonic image; and calculating a volume of the ultrasonic image object according to the three-dimensional model corresponding to the ultrasonic image object.

Another embodiment of the present invention discloses an ultrasonic system, for calculating a volume of ultrasonic image object, comprises a probe, configured to collect a plurality of two-dimensional ultrasonic images; and a processor, configured to obtain the plurality of two-dimensional ultrasonic images, an offset angle, a rotation axis and a frequency of the probe corresponding to the plurality of two-dimensional ultrasonic images, segment a first image including an ultrasonic image object from each two-dimensional ultrasonic image of the plurality of two-dimensional ultrasonic images based on a deep learning structure, determine a contour of the ultrasonic image object according to the first image corresponding to the each two-dimensional ultrasonic image, reconstruct a three-dimensional model corresponding to the ultrasonic image object according to the contour of the ultrasonic image object corresponding to the each two-dimensional ultrasonic image, and calculate a volume of the ultrasonic image object according to the three-dimensional model corresponding to the ultrasonic image object.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
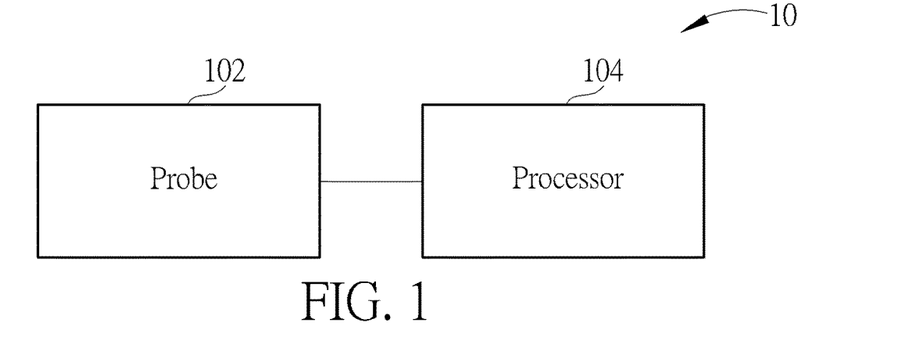
FIG. 1 is a schematic diagram of an ultrasonic system according to an embodiment of the present invention.

Refer to FIG. 1, which is a schematic diagram of an ultrasonic system 10 according to an embodiment of the present invention. The ultrasonic system 10 includes a probe 102 and a processor 104. The ultrasonic system 10 is configured to determine a volume of an ultrasonic image object. The probe 102 is configured to obtain a plurality of two-dimensional ultrasonic images. The ultrasonic system 10 may be utilized for examinations in the medical field, which measures or estimates a volume of a human organ, e.g. a uterus, a prostate or a bladder, with an ultrasonic reflection method. In an embodiment, the probe 102 includes a positioning device for collecting the two-dimensional ultrasonic images and corresponding positioning information. The processor 104 is configured to obtain the two-dimensional ultrasonic images and the corresponding positioning information from the probe 102, e.g. an offset angle, a rotation axis and a frequency of the probe, i.e. the probe 102 may be utilized for scanning the human organs from different offset angles to obtain the two-dimensional ultrasonic images. The processor 104 is configured to segment a first image including an ultrasonic image object from each two-dimensional ultrasonic image of the two-dimensional ultrasonic images based on a deep learning structure, and calculate a volume of the ultrasonic image object according to the first image corresponding to each of the two-dimensional ultrasonic images and a three-dimensional model corresponding to the ultrasonic image object. Therefore, the accuracy of the measured volume of the ultrasonic image object is improved according to the deep learning structure and the three-dimensional model of the ultrasonic system 10 according to an embodiment of the present invention.

Figure 2:
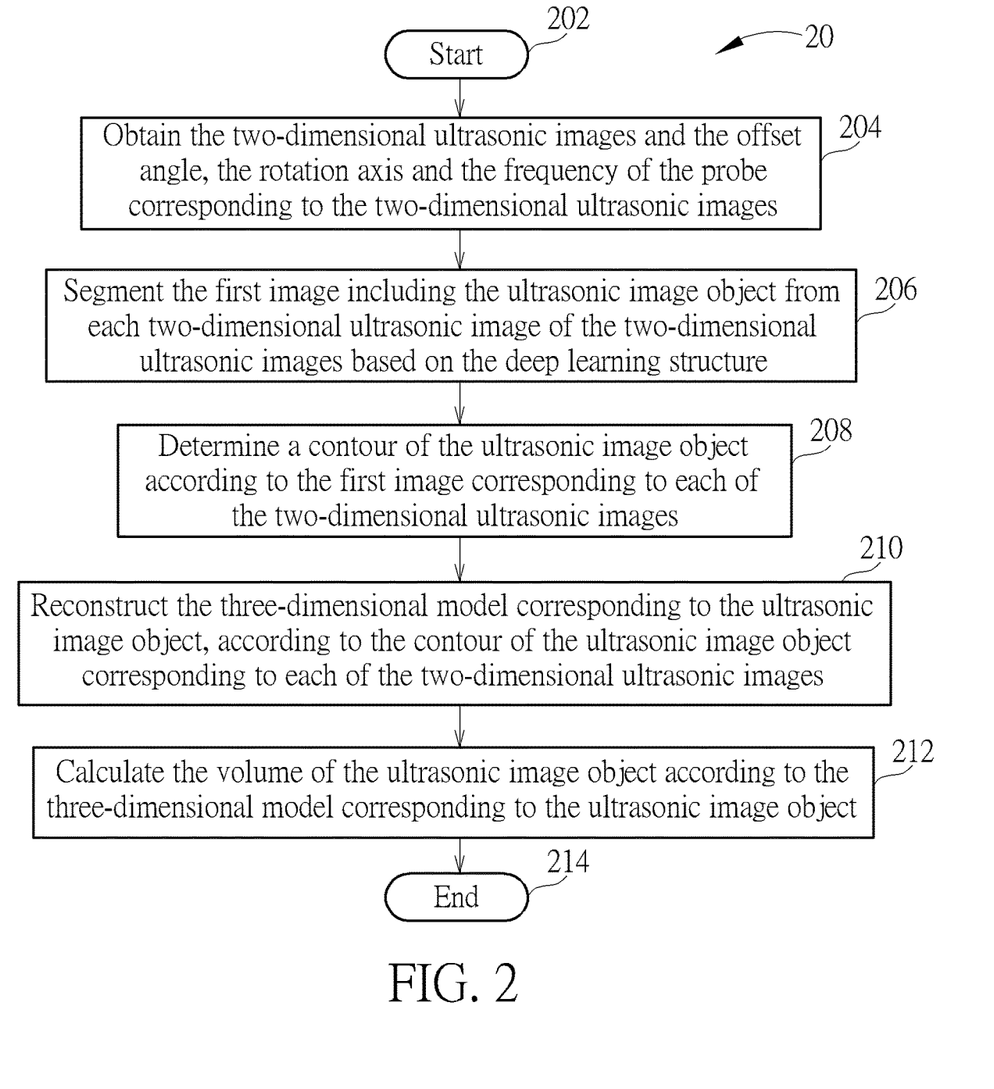
FIG. 2 is a schematic diagram of a volume acquisition method for an ultrasonic image object according to an embodiment of the present invention.

In detail, please refer to FIG. 2, which is a schematic diagram of a volume acquisition method 20 for the ultrasonic image object according to an embodiment of the present invention. As shown in FIG. 2, the volume acquisition method 20 for the ultrasonic image object includes the following steps:

Step 202: Start.

Step 204: Obtain the two-dimensional ultrasonic images and the offset angle, the rotation axis and the frequency of the probe corresponding to the two-dimensional ultrasonic images.

Step 206: Segment the first image including the ultrasonic image object from each two-dimensional ultrasonic image of the two-dimensional ultrasonic images based on the deep learning structure.

Step 208: Determine a contour of the ultrasonic image object according to the first image corresponding to each of the two-dimensional ultrasonic images.

Step 210: Reconstruct the three-dimensional model corresponding to the ultrasonic image object, according to the contour of the ultrasonic image object corresponding to each of the two-dimensional ultrasonic images.

Step 212: Calculate the volume of the ultrasonic image object according to the three-dimensional model corresponding to the ultrasonic image object.

Step 214: End.

First, in step 204, the ultrasonic system 10 may utilize the probe 102 to collect the two-dimensional ultrasonic images and the offset angle, the rotation axis and the frequency of the probe 102 corresponding to the two-dimensional ultrasonic images to increase characteristics of the ultrasonic image object in the two-dimensional ultrasonic images. More specifically, the offset angle, the rotation axis and the frequency of the probe 102 may be utilized for establishing the three-dimensional model of the ultrasonic image object.

Then, in step 206, the ultrasonic system 10 segments the first image including the ultrasonic image object from each two-dimensional ultrasonic image of the two-dimensional ultrasonic images based on the deep learning structure. In an embodiment, the ultrasonic system 10 according to an embodiment of the present invention may segment the first image including the ultrasonic image object from each of the two-dimensional ultrasonic images based on a deep learning structure for semantic segmentation of in a U-Net network structure, wherein the deep learning structure for semantic segmentation classifies each of pixels in a given image to obtain a target image.

In detail, the ultrasonic system 10 according to an embodiment of the present invention adopts the deep learning structure and a self-learning method to detect a preliminary contour and a location of the ultrasonic image object according to the two-dimensional ultrasonic images and the probe corresponding to the two-dimensional ultrasonic images, so as to position the ultrasonic image object and segment the first image including the ultrasonic image object in the two-dimensional ultrasonic images. Notably, the deep learning structure of the ultrasonic system 10 according to an embodiment of the present invention is not limited to the U-Net network structure; other structures which may detect the ultrasonic image object in the two-dimensional ultrasonic images are applicable to the present invention.

Since a computation of the U-Net network structure for segmenting the ultrasonic image object in the two-dimensional ultrasonic images is too high, the ultrasonic system 10 according to an embodiment of the present invention proportionally shrinks the deep learning structure and embeds the deep learning structure into a machine of the ultrasonic system 10 to finish the positioning step of the ultrasonic image object.

Figure 3:
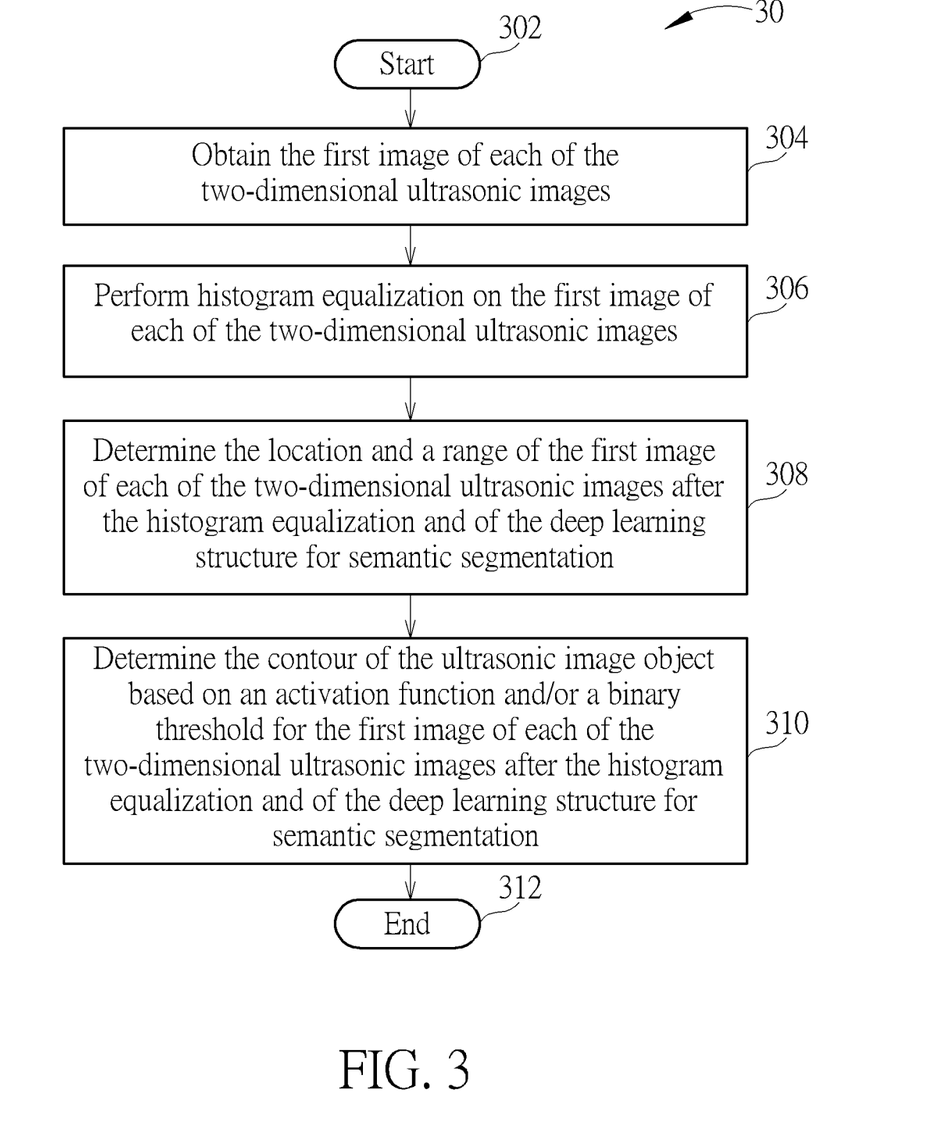
FIG. 3 is a schematic diagram of a contour determination method according to an embodiment of the present invention.

In step 208, the ultrasonic system 10 is configured to determine the contour and the location of the ultrasonic image object based on the first image of each of the two-dimensional ultrasonic images obtained in step 206. In an embodiment, the ultrasonic system 10 is configured to determine the preliminary contour and the location of the ultrasonic image object based on a contour determination method 30. In detail, refer to FIG. 3, which is a schematic diagram of the contour determination method 30 according to an embodiment of the present invention. The contour determination method 30 includes the following steps:

Step 302: Start.

Step 304: Obtain the first image of each of the two-dimensional ultrasonic images.

Step 306: Perform histogram equalization on the first image of each of the two-dimensional ultrasonic images.

Step 308: Determine the location and a range of the first image of each of the two-dimensional ultrasonic images after the histogram equalization and of the deep learning structure for semantic segmentation.

Step 310: Determine the contour of the ultrasonic image object based on an activation function and/or a binary threshold for the first image of each of the two-dimensional ultrasonic images after the histogram equalization and of the deep learning structure for semantic segmentation.

Step 312: End.

In order to precisely determine the contour and the location of the ultrasonic image object in the two-dimensional ultrasonic images, the ultrasonic system 10 according to an embodiment of the present invention may determine the contour of the ultrasonic image object based on two different methods of the contour determination method 30. In step 304, the first image is obtained based on the deep learning structure, wherein the preliminary contour of the object is included in the first image. In step 306, the first image of each of the two-dimensional ultrasonic images is performed with the histogram equalization to increase a contrast of the first image. In step 308, the deep learning structure for semantic segmentation is utilized for determining the location and the range of the object in the first image of each of the two-dimensional ultrasonic images after the histogram equalization. Then, in step 310, the contour of the ultrasonic image object is determined with the activation function and/or the binary threshold for the first image of each of the two-dimensional ultrasonic images after the deep learning structure for semantic segmentation, wherein the activation function determines the contour and the location of the ultrasonic image object by expanding the contour of the ultrasonic image object outwardly, which is obtained in step 210; the binary threshold determines the contour and the location of the ultrasonic image object according to the contour of the ultrasonic image object obtained in step 210.

Notably, the above contour determination method 30 may simultaneously adopt the activation function and the binary threshold to determine the contour and the location of the ultrasonic image object. Alternatively, in another embodiment, the ultrasonic system 10 according to an embodiment of the present invention may determine the contour and the location of the ultrasonic image object according to the activation function or the binary threshold, which is within the scope of the present invention.

Figure 4:
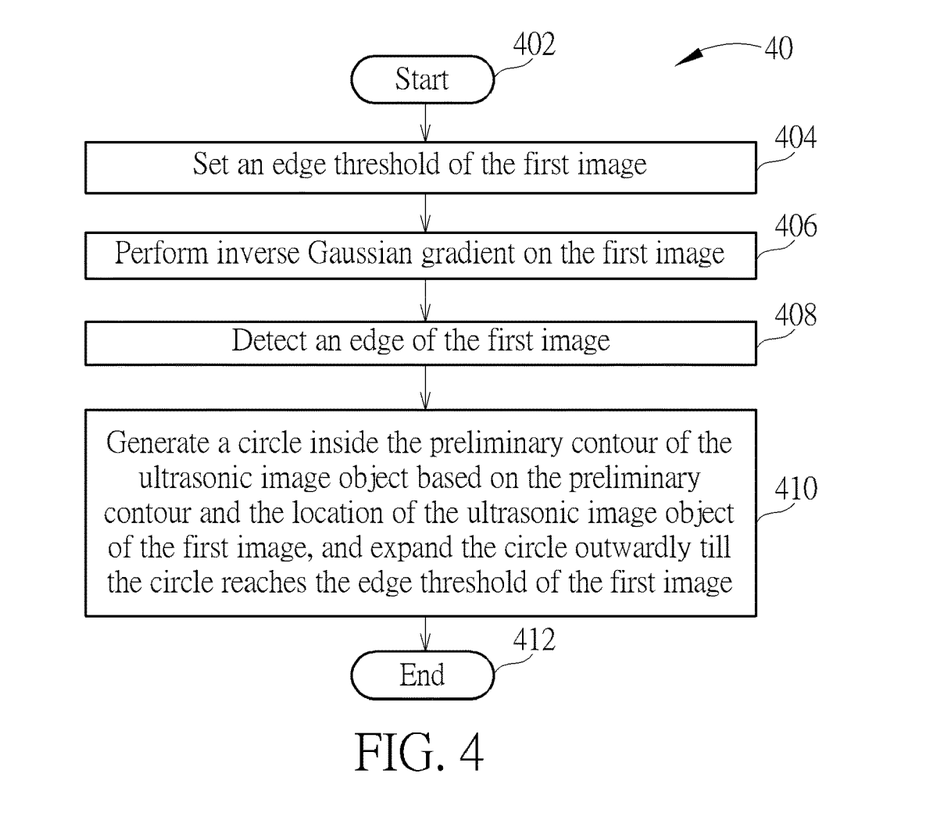
FIG. 4 and FIG. 5 are schematic diagrams of a contour determination method according to another embodiment of the present invention.

Regarding the method of determining the contour and the location of the ultrasonic image object based on the activation function, please refer to FIG. 4, which is a schematic diagram of a contour determination method 40 according to an embodiment of the present invention. The contour determination method 40 determines the contour and the location of the ultrasonic image object based on the activation function, which includes the following steps:

Step 402: Start.

Step 404: Set an edge threshold of the first image.

Step 406: Perform inverse Gaussian gradient on the first image.

Step 408: Detect an edge of the first image.

Step 410: Generate a circle inside the preliminary contour of the ultrasonic image object based on the preliminary contour and the location of the ultrasonic image object of the first image, and expand the circle outwardly till the circle reaches the edge threshold of the first image.

Step 412: End.

In step 404, the edge threshold of the first image is set as a stopping point when the preliminary contour expands outwardly. In step 406, the inverse Gaussian gradient is performed on the first image to blur the first image. In step 408, the edge of the image is detected. In step 410, according to the preliminary contour and location of the ultrasonic image object in the first image, the circle inside the preliminary contour of the ultrasonic image object is generated and the circle is expanded outwardly till reaching the edge threshold of the first image, i.e. the stopping point. Therefore, the ultrasonic system 10 according to an embodiment of the present invention may determine the contour and the location of the ultrasonic image object based on the preliminary contour of the ultrasonic image object and the contour determination method 40.

Figure 5:
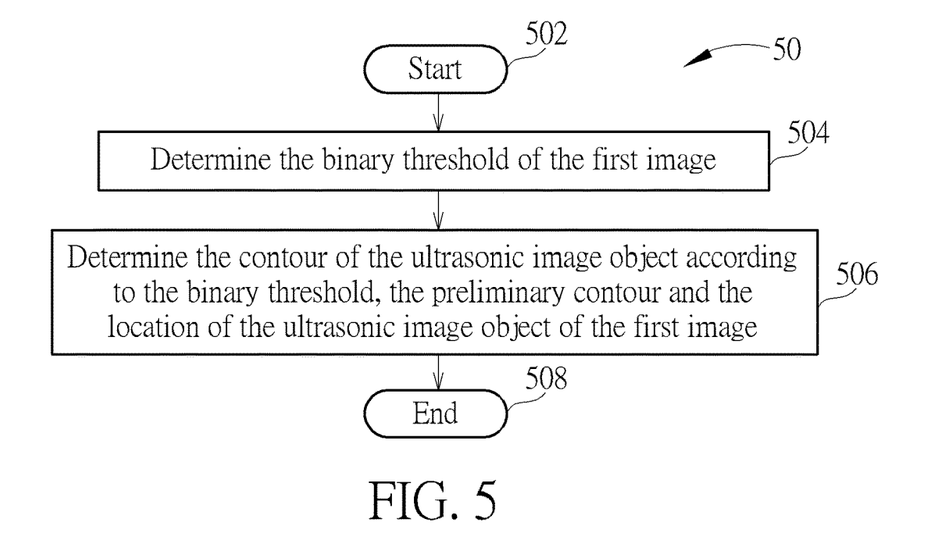

On the other hand, regarding the method of determining the contour and the location of the ultrasonic image object based on the binary threshold, please refer to FIG. 5, which is a schematic diagram of a contour determination method 50 according to an embodiment of the present invention. The contour determination method 50 determines the contour and the location of the ultrasonic image object method based on the binary threshold, which includes the following steps:

Step 502: Start.

Step 504: Determine the binary threshold of the first image.

Step 506: Determine the contour of the ultrasonic image object according to the binary threshold, the preliminary contour and the location of the ultrasonic image object of the first image.

Step 508: End.

Based on the contour determination method 50, the ultrasonic system 10 determines the binary threshold of the first image in step 504, e.g. an 8-bit image has a grayscale value 255. In step 506, the first image is divided into two colors (e.g. black and white) based on the binary threshold, the contour of the ultrasonic image object is determined according to the preliminary contour and location of the ultrasonic image object of the first image after the histogram equalization. In an embodiment, when the ultrasonic image object is a bladder, and the grayscale value of the binary threshold of the 8-bit image is 128, pixels in the first image with grayscale value over 128 are classified as a bladder and pixels with grayscale value lower than 128 are classified as not a bladder, such that the contour determination method 50 may distinguish the bladder in the first image (i.e. the ultrasonic image object) and compare with the preliminary contour of the ultrasonic image object. Therefore, the ultrasonic system 10 according to an embodiment of the present invention may determine the contour and the location of the ultrasonic image object based on the preliminary contour of the ultrasonic image object and the contour determination method 50.

Notably, domain parameters of the above contour determination methods 40, 50 are determined based on an exhaustive method, such that an optimal domain parameter of the ultrasonic image object is determined.

Figure 6:
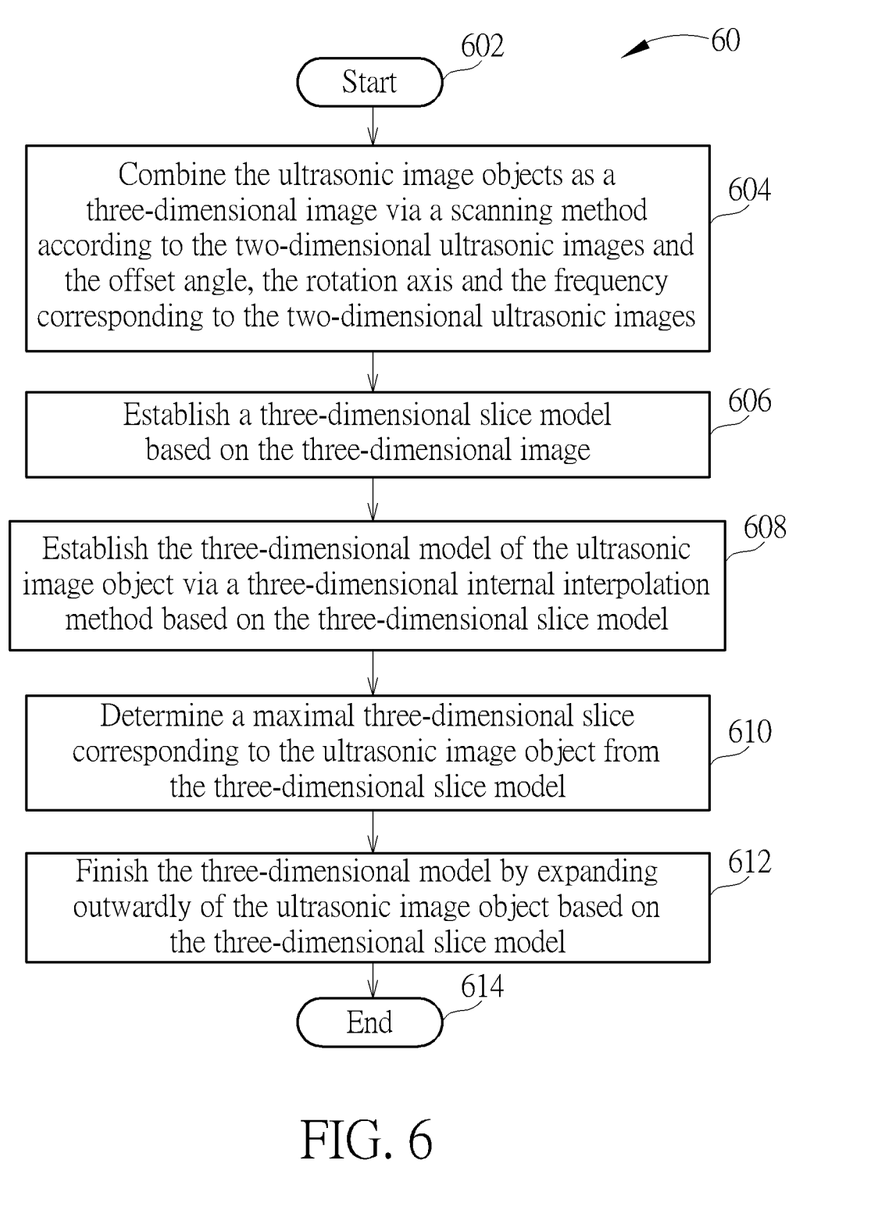
FIG. 6 is a schematic diagram of a three-dimensional modeling method according to an embodiment of the present invention.

After the contour of the ultrasonic image object corresponding to each of the two-dimensional ultrasonic images is determined in step 208, the three-dimensional model corresponding to the ultrasonic image object is reconstructed based on the contour of the ultrasonic image object determined in step 210. Regarding steps of reconstructing the three-dimensional model corresponding to the ultrasonic image object, please refer to FIG. 6, which is a schematic diagram of a three-dimensional modeling method 60 according to an embodiment of the present invention. The three-dimensional modeling method 60 includes the following steps:

Step 602: Start.

Step 604: Combine the ultrasonic image objects as a three-dimensional image via a scanning method according to the two-dimensional ultrasonic images and the offset angle, the rotation axis and the frequency corresponding to the two-dimensional ultrasonic images.

Step 606: Establish a three-dimensional slice model based on the three-dimensional image.

Step 608: Establish the three-dimensional model of the ultrasonic image object via a three-dimensional internal interpolation method based on the three-dimensional slice model.

Step 610: Determine a maximal three-dimensional slice corresponding to the ultrasonic image object from the three-dimensional slice model.

Step 612: Finish the three-dimensional model by expanding outwardly of the ultrasonic image object based on the three-dimensional slice model.

Step 614: End.

In step 604, the ultrasonic system 10 combines multiple two-dimensional ultrasonic images, which are of a sequence, as the three-dimensional image via the scanning method according to each first image including the ultrasonic image object obtained in step 206 and the corresponding rotation axis and the frequency corresponding to the probe 102. In an embodiment, the scanning method may be a sector scan or a sagittal scan, which combines consecutive ultrasonic image objects as the three-dimensional ultrasonic images. In other words, the ultrasonic system 10 may establish the three-dimensional ultrasonic image based on multiple two-dimensional ultrasonic images including the ultrasonic image objects, of one sequence (e.g. 50 images), the offset angle, the rotation axis, the frequency corresponding to the probe 102 and a formula (1), wherein the formula (1) projects Y-axis of the ultrasonic image object onto Z-axis. And the formula (1) is:

$$\sum_{i=0}^{EndofSequenceImage} z_i = \sum_{i=0}^{EndofSequenceImage} 640 + (\cos Degree_i * objectDown_i) \quad (1)$$

In formula (1), i denotes i-th ultrasonic image object of the sequence, 640 denotes horizontal pixel value of resolution, $Degree_i$ denotes the offset angle when the probe 102 performs scanning, $objectDown_i$ denotes a lower section of a bottom plane of the ultrasonic image object. Notably, the horizontal resolution of the two-dimensional image of the ultrasonic system 10 is not limited to 640.

In step 606, the three-dimensional slice model is established based on the three-dimensional ultrasonic image, i.e. the three-dimensional ultrasonic image is sliced into multiple three-dimensional slices. Then, in step 608, the three-dimensional model of the ultrasonic image object is established with the three-dimensional internal interpolation method based on the three-dimensional slice model, which makes up missing parts of the ultrasonic image object, such that a complete ultrasonic image object model is finished.

Figure 7:
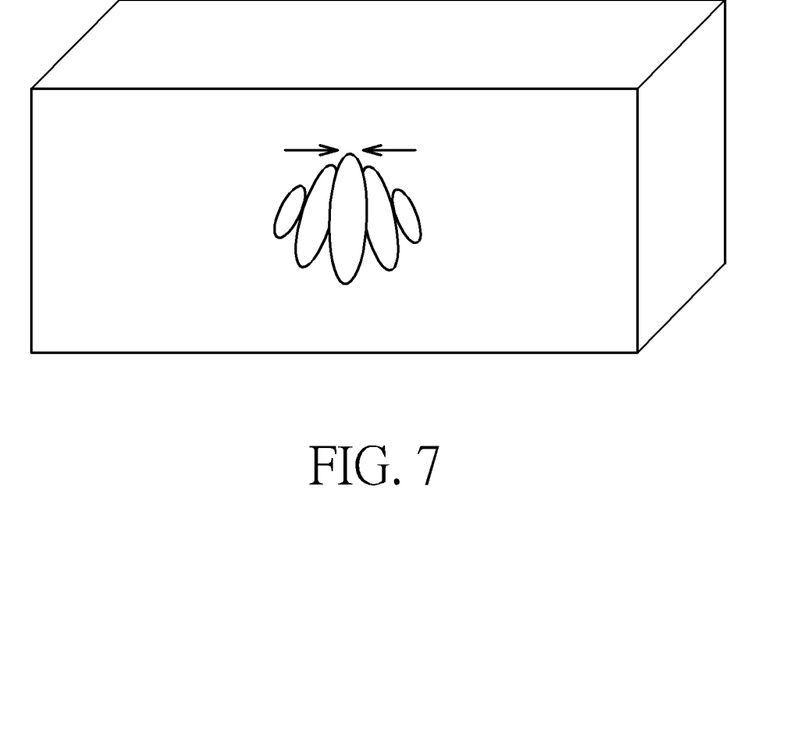
FIG. 7 is a schematic diagram of a three-dimensional inner interpolation according to an embodiment of the present invention.

In an embodiment, the ultrasonic system 10 may calculate a maximal distance between two three-dimensional slices and perform the three-dimensional internal interpolation method on the two three-dimensional slices. FIG. 7 is a schematic diagram of the three-dimensional inner interpolation performed on the ultrasonic image object according to an embodiment of the present invention. In a three-dimensional space, the ultrasonic system 10 may utilize the left-most and the right-most three-dimensional slices to inwardly perform the three-dimensional internal interpolation method to establish the ultrasonic image object model.

Figure 8:
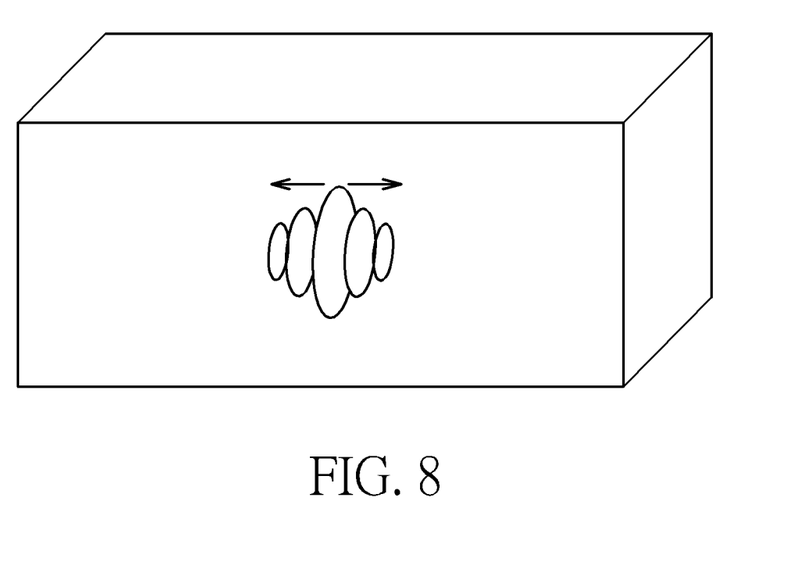
FIG. 8 is a schematic diagram of a three-dimensional external interpolation according to an embodiment of the present invention.

However, since the accuracy of the three-dimensional internal interpolation method may be affected by a scanning speed and a shape of the ultrasonic image object (e.g. a shape bladder shape is oval when under examination), in step 610, the ultrasonic system 10 determines the maximal three-dimensional slice from the three-dimensional slices, and in step 612, the three-dimensional model is finished based on the maximal three-dimensional slice by expanding the ultrasonic image object outwardly, as shown in FIG. 8, which is a schematic diagram of a three-dimensional external interpolation performed on the ultrasonic image object according to an embodiment of the present invention, i.e. expanding the maximal three-dimensional slice outwardly in the middle of FIG. 8 to finish the three-dimensional model.

Therefore, the three-dimensional model of the ultrasonic image object may be accurately established based on the three-dimensional modeling method 60, such that the ultrasonic system 10 may determine the volume of the ultrasonic image object based on the three-dimensional model corresponding to the ultrasonic image object determined in step 212.

The above embodiments illustrate that a volume acquisition method for an object in ultrasonic image and related ultrasonic system of the present invention may detect the ultrasonic image object via the deep learning structure to accurately and efficiently calculate the volume of the ultrasonic image object by establishing the three-dimensional model. In addition, according to different requirements, volume acquisition method for an object in ultrasonic image and related ultrasonic system of the present invention may be utilized for calculating image volume of computed tomography (CT) system or magnetic resonance imaging (MRI) system.

In summary, embodiments of the present invention provides a volume acquisition method for an object in ultrasonic image and related ultrasonic system, which combines the deep learning structure and establishes the three-dimensional model to accurately and efficiently calculate a volume of the ultrasonic image object and improve the accuracy of detection.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An object volume acquisition method of an ultrasonic image, for a probe of an ultrasonic system, wherein the volume acquisition method of the object in the ultrasonic image comprising:
    collecting, by the probe, a plurality of two-dimensional ultrasonic images;
    obtaining the plurality of two-dimensional ultrasonic images, an offset angle, a rotation axis and a frequency of the probe corresponding to the plurality of two-dimensional ultrasonic images;
    segmenting a first image including an ultrasonic image object from each two-dimensional ultrasonic image of the plurality of two-dimensional ultrasonic images based on a deep learning structure;
    determining a contour of the ultrasonic image object according to the first image corresponding to the each two-dimensional ultrasonic image;
    reconstructing a three-dimensional model corresponding to the ultrasonic image object according to the contour of the ultrasonic image object corresponding to the each two-dimensional ultrasonic image; and
    calculating a volume of the ultrasonic image object according to the three-dimensional model corresponding to the ultrasonic image object;
    wherein the deep learning structure is a U-Net network structure for determining a preliminary contour and a location of the ultrasonic image object of the first image according to the offset angle, the rotation axis and the frequency of the probe corresponding to the plurality of two-dimensional ultrasonic images;
    wherein the step of determining the contour of the ultrasonic image object according to the first image corresponding to the each two-dimensional ultrasonic image includes:
    setting an edge threshold;
    detecting an edge of the first image; and
    generating a circle inside the preliminary contour of the ultrasonic image object based on the preliminary contour and the location of the ultrasonic image object of the first image, and expanding the circle outwardly till the circle reaches the edge threshold of the first image.

2. The object volume acquisition method in the ultrasonic image of claim 1, wherein the first image is performed with histogram equalization before setting the edge threshold of the first image.

3. The object volume acquisition method in the ultrasonic image of claim 1, wherein the step of determining the contour of the ultrasonic image object according to the first image corresponding to the each two-dimensional ultrasonic image includes:
  performing histogram equalization on the first image;
  determining a binary threshold of the first image; and
  determining the contour of the ultrasonic image object according to the binary threshold, the preliminary contour and the location of the ultrasonic image object of the first image.

4. The object volume acquisition method in the ultrasonic image of claim 1, wherein the step of reconstructing the three-dimensional model corresponding to the ultrasonic image object according to the contour of the ultrasonic image object corresponding to the each two-dimensional ultrasonic image includes:
  combining the plurality of ultrasonic image objects as a three-dimensional image via a scanning method according to the plurality of two-dimensional ultrasonic images and the offset angle, the rotation axis and the frequency corresponding to the plurality of two-dimensional ultrasonic images;
  establishing a three-dimensional slice model based on the three-dimensional image; and
  establishing the three-dimensional model of the ultrasonic image object via a three-dimensional internal interpolation method based on the three-dimensional slice model.

5. The object volume acquisition method in the ultrasonic image of claim 4, wherein the step of establishing the three-dimensional model of the ultrasonic image object via the three-dimensional internal interpolation method based on the three-dimensional slice model includes:
  determining a maximal three-dimensional slice corresponding to the ultrasonic image object from the three-dimensional slice model; and
  finishing the three-dimensional model by expanding outwardly of the ultrasonic image object based on the three-dimensional slice model.

6. An ultrasonic system, for calculating a volume of ultrasonic image object, comprising:
  a probe, configured to collect a plurality of two-dimensional ultrasonic images; and
  a processor, configured to obtain the plurality of two-dimensional ultrasonic images, an offset angle, a rotation axis and a frequency of the probe corresponding to the plurality of two-dimensional ultrasonic images, segment a first image including an ultrasonic image object from each two-dimensional ultrasonic image of the plurality of two-dimensional ultrasonic images based on a deep learning structure, determine a contour of the ultrasonic image object according to the first image corresponding to the each two-dimensional ultrasonic image, reconstruct a three-dimensional model corresponding to the ultrasonic image object according to the contour of the ultrasonic image object corresponding to the each two-dimensional ultrasonic image, and calculate a volume of the ultrasonic image object according to the three-dimensional model corresponding to the ultrasonic image object;
  wherein the deep learning structure is a U-Net network structure for determining a preliminary contour and a location of the ultrasonic image object of the first image according to the offset angle, the rotation axis and the frequency of the probe corresponding to the plurality of two-dimensional ultrasonic images;
  wherein the processor is configured to set an edge threshold, detect an edge of the first image, generate a circle inside the preliminary contour of the ultrasonic image object based on the preliminary contour and the location of the ultrasonic image object of the first image, and expand the circle outwardly till the circle reaches the edge threshold of the first image.

7. The ultrasonic system of claim 6, wherein before the edge threshold of the first image is set, the processor is configured to perform histogram equalization on the first image.

8. The ultrasonic system of claim 6, wherein the processor is configured to perform histogram equalization on the first image, determine a binary threshold of the first image and determine the contour of the ultrasonic image object according to the binary threshold, the preliminary contour and the location of the ultrasonic image object of the first image.

9. The ultrasonic system of claim 6, wherein the processor is configured to combine the plurality of ultrasonic image objects as a three-dimensional image via a scanning method according to the plurality of two-dimensional ultrasonic images and the offset angle, the rotation axis and the frequency corresponding to the plurality of two-dimensional ultrasonic images, establish a three-dimensional slice model based on the three-dimensional image, and establish the three-dimensional model of the ultrasonic image object via a three-dimensional interpolation method based on the three-dimensional slice model.

10. The ultrasonic system of claim 9, wherein the processor is configured to determine a maximal three-dimensional slice corresponding to the ultrasonic image object from the three-dimensional slice model, and finish the three-dimensional model by expanding outwardly of the ultrasonic image object based on the three-dimensional slice model.

* * * * *